US012751839B2

(12) United States Patent
Goldfarb et al.

(10) Patent No.: US 12,751,839 B2
(45) Date of Patent: Oct. 6, 2026

(54) POWERED-ON PASSIVE KNEE PROSTHESIS SYSTEM

(71) Applicant: Vanderbilt University, Nashville, TN (US)

(72) Inventors: Michael Goldfarb, Nashville, TN (US); Steven C. Culver, Nashville, TN (US); Leo G. Vailati, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 896 days.

(21) Appl. No.: 18/173,983

(22) Filed: Feb. 24, 2023

(65) Prior Publication Data

US 2023/0270571 A1 Aug. 31, 2023

Related U.S. Application Data

(60) Provisional application No. 63/313,979, filed on Feb. 25, 2022.

(51) Int. Cl.

*A61F 2/64* (2006.01)
*A61F 2/60* (2006.01)
*A61F 2/70* (2006.01)
*A61F 2/66* (2006.01)

(52) U.S. Cl.

CPC .......... *A61F 2/64* (2013.01); *A61F 2002/607* (2013.01); *A61F 2002/6614* (2013.01); *A61F 2002/701* (2013.01); *A61F 2002/704* (2013.01)

(58) Field of Classification Search

CPC .................. A61F 2/64; A61F 2002/607; A61F 2002/6614; A61F 2002/701; A61F 2002/704; A61F 2002/5033; A61F 2002/6818; A61F 2/60; A61F 2/74; A61F 2002/7625; A61F 2002/7635; A61F 2002/764; A61F 2002/7645; A61F 2/70

See application file for complete search history.

(56) References Cited

U.S. PATENT DOCUMENTS 10,111,762 B2 10/2018 Goldfarb
10,772,743 B2 9/2020 Seifert
2011/0098828 A1* 4/2011 Balboni .................... A61F 2/60 623/40
2021/0059841 A1* 3/2021 Goldfarb ................. A61F 2/644
2023/0270571 A1* 8/2023 Goldfarb ................... A61F 2/74 623/39

* cited by examiner

*Primary Examiner* — Bruce E Snow
(74) *Attorney, Agent, or Firm* — NIXON PEABODY LLP

(57) ABSTRACT

A knee prosthesis system including a knee prosthesis, an actuator and a controlling unit. The knee prosthesis includes a thigh segment and a shank segment. The actuator rotatably connects the shank segment and the thigh segment. The actuator is configured to controllably assume a powered knee behavior to generate knee motion or a passive knee behavior to resist knee motion. The controlling unit includes a finite-state control structure. The controlling unit electrically communicates with the actuator. The control structure includes at least three passive states and at least one powered state. The passive states include a passive stance-resistance state, a swing-flexion state, and a swing-extension state and the at least one powered state includes at least one of a swing-assistance state, a stance-assistance state, and a powered-swing state.

16 Claims, 13 Drawing Sheets

POWERED-ON PASSIVE KNEE PROSTHESIS SYSTEM

CROSS-REFERENCE TO RELATED APPLICATIONS

This application claims priority to and the benefit of U.S. Provisional Application No. 63/313,979 filed Feb. 25, 2022 and entitled "ECT Passive and Powered Control," the contents of which are herein incorporated by reference in their entirety.

GOVERNMENT LICENSE RIGHTS

This invention was made with government support under NSF Grant No. 2018260077. The government has certain rights in the invention.

FIELD OF THE INVENTION

This application is directed to knee prosthesis and, more specifically, is directed to a knee prosthesis that has both passive and powered knee behavior.

BACKGROUND OF THE INVENTION

Powered knee prostheses have begun to emerge, although effective methods of coordinating the delivery of power with the movement and movement intent of the user have not been established. Knee prostheses have traditionally been energetically passive devices, which cannot in and of themselves provide powered movement. Rather, a passive knee can only move by physical coupling to a user. In this manner, the movement of a passive knee prosthesis is fundamentally and physically coordinated with the person using it. Conversely, a powered prosthesis has volition, and therefore can move independently of the person wearing it. As such, there is no fundamental guarantee that the powered knee prosthesis will move in concert with the person wearing it. Therefore, there is a need to control the powered movements of a knee prosthesis so that the powered movements of the prosthesis are highly coordinated with the movements of the wearer.

SUMMARY

According to one aspect of the present disclosure, a knee prosthesis system comprises a knee prosthesis, at least one actuator, and a controlling unit. The knee prosthesis includes a thigh segment and a shank segment. The at least one actuator rotatably connects the shank segment and the thigh segment, which may be, for example, a rotary or linear type. The at least one actuator is configured to controllably assume a powered knee behavior to generate knee motion or a passive knee behavior to resist knee motion. The controlling unit includes a finite-state control structure. The controlling unit electrically communicates with the at least one actuator. The control structure comprises at least three passive states and at least one powered state. The at least three passive states include a passive stance-resistance state, a passive swing-flexion state, and a passive swing-extension state. The at least one powered state includes at least one of a powered swing-assistance state, a powered stance-assistance state, and a powered-swing state.

According to a configuration of the above implementation, the passive stance-resistance state provides a high resistance against knee flexion, the passive swing-flexion state provides relative low resistance against knee flexion, and the passive swing-extension state provides a low resistance against knee extension that increases substantially as a knee nears full extension. The powered swing-assistance state provides an assistive torque that flexes a knee joint, the powered stance-assistance state provides an assistive torque that extends the knee joint, and the powered-swing state provides a prescribed knee joint motion. In addition to a high resistance against knee flexion, the stance-resistance state can provide either a low or high resistance against knee extension.

According to another configuration of the above implementation, the at least one powered state is the powered swing-assistance state. The controlling unit selects the swing-assistance state from the passive swing-flexion state based on detection of an entry condition, and the controlling unit exits the powered swing-assistance state into the passive swing-extension state upon detection of an exit condition. The entry condition may select the powered swing-assistance state from the passive swing-flexion state by including at least a detection of estimated walking speed less than a predetermined speed, and the exit condition may exit the powered swing-assistance state into the passive swing-extension state by including at least a detection of a knee extension. The resistance in the passive swing-flexion state and assistance in the powered swing-assistance state may provide a net energy dissipation at a knee by increasing continuously and monotonically as a function of estimated walking speed.

According to a configuration of the above implementation, the at least one powered state is the powered stance-assistance state. The controlling unit selects the powered stance-assistance state from the passive stance-resistance state based on detection of an entry condition, and the controlling unit exits the powered stance-assistance state into the passive stance-resistance state upon detection of an exit condition. The entry condition may select the powered stance-assistance state from the passive stance-resistance state by including at least detection of a knee joint extension, and the exit condition may exit the powered stance-assistance state into the passive stance-resistance state by including at least detection of knee joint flexion. The powered stance-assistance state may provide an assistive knee extension torque that is a function of at least a measured force in the knee prosthesis and a measured angular velocity of the thigh segment in another embodiment. An assistive extension knee torque may be provided that is proportional to the estimated hip torque exerted by a user and estimated thigh angular velocity in another embodiment.

According to another configuration of the above implementation, the at least one powered state is a powered-swing state. The controller selects the powered-swing state from the passive swing-flexion state based on detection of an entry condition, and the controller exits the powered-swing state into the passive stance-resistance state upon detection of an exit condition. The entry condition may select the powered-swing state from the passive swing-flexion state by including at least detection of a full knee joint extension when the knee prosthesis is unloaded, or axial acceleration of the shank segment is above a threshold value when the knee prosthesis is unloaded, and wherein the exit condition includes at least detection of prosthesis loading. Flexion knee assistance may be a function of thigh angular velocity such that a knee will not initiate flexion until a thigh begins to flex in another embodiment in a further embodiment.

According to a configuration of the above implementation, the at least one powered state includes at least two of the powered swing-assistance state, the powered stance-assistance state, and the powered-swing state. In another embodiment, the at least one powered state includes all of the powered swing-assistance state, the powered stance-assistance state, and the powered-swing state.

According to another configuration of the above implementation, the passive swing-flexion assistance is a function of knee angle such that the flexion assistance torque is not provided until the user begins to flex the knee.

According to a configuration of the above implementation, the at least one actuator is a rotary actuator. According to another configuration of the above implementation, the at least one actuator is a linear actuator.

According to one aspect of the present disclosure, a lower limb prosthesis comprises a foot prosthesis and a knee prosthesis system. The knee prosthesis system includes a thigh segment, a shank segment, at least one actuator and a controlling unit. The at least one actuator rotatably connects the shank segment and the thigh segment. The at least one actuator is configured to controllably assume a powered knee behavior to generate knee motion or a passive knee behavior to resist knee motion. The controlling unit includes a finite-state control structure. The controlling unit electrically communicates with the at least one actuator. The control structure comprises at least three passive states and at least one powered state. The at least three passive states include a passive stance-resistance state, a passive swing-flexion state, and a passive swing-extension state. The at least one powered state includes at least one of a powered swing-assistance state, a powered stance-assistance state, and a powered-swing state.

The above summary is not intended to represent each embodiment or every aspect of the present invention. Additional features and benefits of the present invention are apparent from the detailed description and figures set forth below.

BRIEF DESCRIPTION OF DRAWINGS

Other advantages of the invention will become apparent upon reading the following detailed description and upon reference to the drawings in which.

Figure 1:
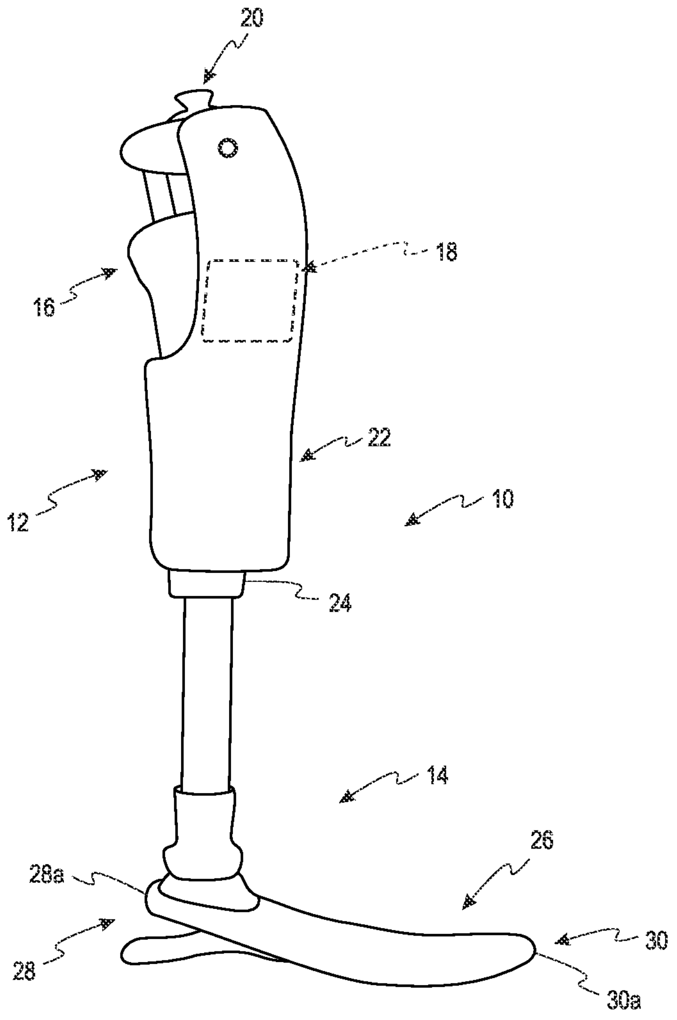
FIG. 1 is a lower limb prosthesis, including a knee prosthesis and a foot prosthesis, according to one embodiment.

While the invention is susceptible to various modifications and alternative forms, specific embodiments thereof have been shown by way of example in the drawings and will herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

DETAILED DESCRIPTION

This invention is directed to a control structure for a powered knee prosthesis that selectively layers powered behaviors onto underlying passive behaviors, and in doing so facilitates highly coordinated movement between a user and the knee prosthesis, and also assures the user with a high degree of agency over movement. This high degree of coordination is provided by utilizing strictly passive control for most activities, as is provided by current passive prosthetic knees, and providing powered assistance only for those activities that require powered assistance. Furthermore, powered assistance is provided in a manner that physically couples a user's inputs with the provided assistance, such that the knee prosthesis provides powered assistance as a reaction to the user's inputs into an otherwise passive system. The controlling unit provides power-assisted behavior appropriate for a wide range of activities, including level-ground, up-slope, down-slope, up-stairs, down-stairs, and backwards walking, as well as stand-to-sit and sit-to-stand transitions.

This application describes a knee prosthesis system including comprising a knee prosthesis, at least one actuator and a controlling unit. The knee prosthesis includes a thigh segment and a shank segment. The at least one actuator rotatably connects the shank segment and the thigh segment. The at least one actuator is configured to controllably assume a powered knee behavior to generate knee motion or a passive knee behavior to resist knee motion. The controlling unit includes a finite-state control structure. The controlling unit electrically communicates with the at least one actuator. The control structure comprises at least three passive states and at least one powered state. The at least three passive states includes a passive stance-resistance state, a passive swing-flexion state, and a passive swing-extension state. The at least one powered state includes at least one of a powered swing-assistance state, a powered stance-assistance state, and a powered-swing state.

One non-limiting example of a lower limb prosthesis that may be used is shown in FIG. 1. The lower limb prosthesis of the present invention facilitates the gait of a user. Referring still to FIG. 1, a lower limb prosthesis 10 is shown that assists a user in discrete activities or tasks such as level walking, up-sloped or down-sloped walking, backward walking, slow walking, standing, sitting (sit-to-stand or stand-to-sit), stair ascent and stair decent. The lower limb prosthesis 10 includes a knee prosthesis system 12 and a foot prosthesis 14. The knee prosthesis 12 includes at least one actuator 16 and a controlling unit 18 in this embodiment. The knee prosthesis includes a thigh segment 20 and a shank segment 22.

The at least one actuator 16 rotatably connects the thigh segment 20 and the shank segment 22. The at least one actuator 16 is configured to controllably assume a powered knee behavior to generate knee motion or a passive knee behavior to resist knee motion. The at least one actuator 16 may be a rotary actuator in one embodiment. In another embodiment, the actuator may be a linear actuator. It is contemplated that other actuators may be used in the knee prosthesis.

The controlling unit 18 includes a finite-state control structure. The controlling unit 18 electrically communicates with the at least one actuator 16. The control structure comprises at least three passive states and at least one powered state. The at least three passive states includes a passive stance-resistance state, a passive swing-flexion state, and a passive swing-extension state. The at least one powered state includes at least one of a powered swing-assistance state, a powered stance-assistance state, and a powered-swing state.

It is contemplated that the powered state may include two of the following: a powered swing-assistance state, a powered stance-assistance state, and a powered-swing state. In another embodiment, the powered state includes all of the following: a powered swing-assistance state, a powered stance-assistance state, and a powered-swing state.

The lower limb prosthesis 10 in one embodiment may include a load cell 24. The load cell 24 in the lower limb prosthesis 10, if used, assists in determining loads on the lower limb prosthesis 10. The load cell 24 is a device that measures forces. In some embodiments a load cell measured moments. Load cells may be purchased for use or may be custom designed and integrated with the lower limb prosthesis. A non-limiting example of a load cell that may be used in the lower limb prosthesis is described in U.S. Pat. No. 10,111,762, which is hereby incorporated by reference in its entirety. It is contemplated that other load cells may be used in the lower limb prosthesis.

Referring still to FIG. 1, the foot prosthesis 14 of the lower limb prosthesis 10 includes a foot area 26. The foot area 26 includes a heel portion 28 and a toe portion 30. The heel portion 28 includes a posterior portion 28*a*, while the toe portion 30 includes an anterior portion 30*a*.

Figure 2:
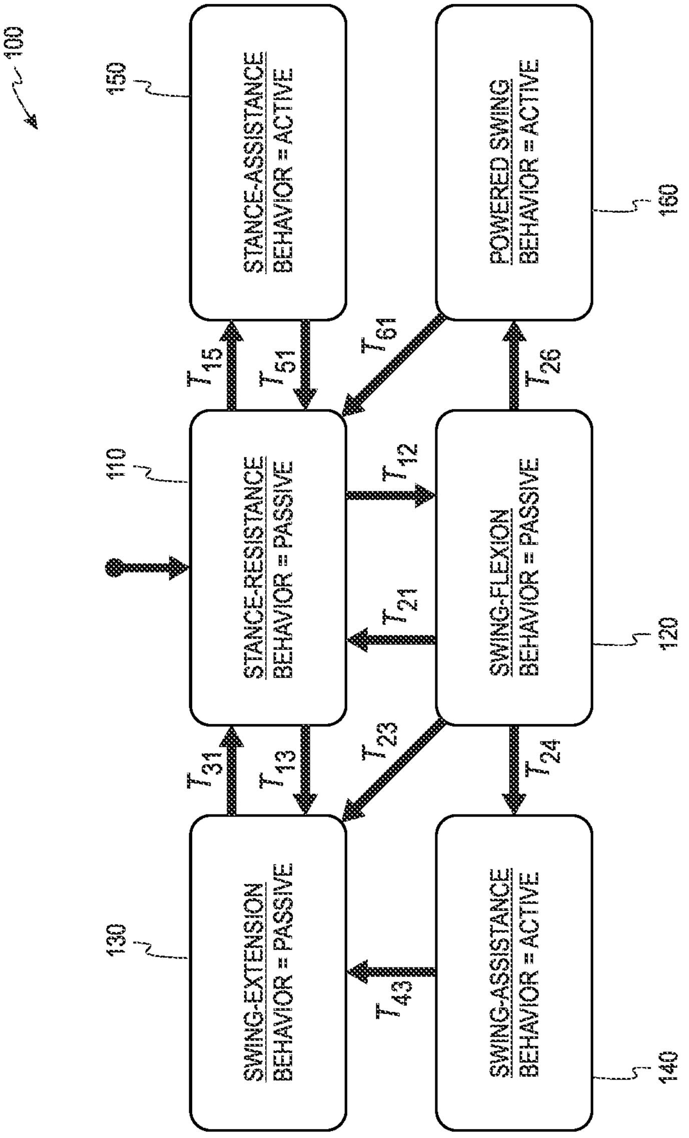
FIG. 2 is a state flow chart of a controlling unit including six states and transitions between them according to one embodiment.

Referring to FIG. 2, a state flow chart 100 of a controlling unit (e.g., controller unit 18) is shown that provides passive and powered functionality across a wide range of activities. This is also referred to as finite-state machine (FSM). Each state in the state flow chart provides a unique behavior that is generalizable across a range of activities, as will be discussed below, which shows each state being utilized in the stateflow of several different activities.

The state flow chart 100 of the controlling unit includes states 110, 120 and 130 that are passive states that provide strictly passive behaviors. The state flow chart 100 of the controlling unit further includes states 140, 150 and 160 that are powered states that provide powered (or assistive or active) behaviors. The passive state behaviors are as follows: (1) in the passive stance-resistance state (state 110), in which the knee provides a high resistance against knee flexion; (2) in the passive swing-flexion state (state 120), in which the knee provides a relatively low resistance against knee flexion; and (3) in the passive swing-extension state (state 130), in which the knee provides a low resistance against extension for most of the range of motion of the knee, with increasing levels of resistance as the knee nears full extension. These three passive states do not employ powered assistance, and as such, the knee prosthesis 12 can only react to movements by a user.

The controlling unit to be used in the knee prosthesis includes at least one of the three powered states shown in FIG. 2. In one embodiment, the knee controller includes all three powered states 140, 150, 60 of FIG. 2, each of which provides state behaviors as follows: (1) in the powered swing-assistance state (state 140), in which the knee provides powered knee flexion assistance; (2) in the powered stance-assistance state (state 150), in which the knee provides powered knee extension assistance; and (3) in the powered-swing state (state 160), in which the knee provides a prescribed knee motion (e.g., a prescribed knee angle trajectory). The knee prosthesis is configured and is capable of being controlled in each of these respective behaviors.

The various transitions between the states 110, 120, 130, 140, 150, 160 are shown in FIG. 2. Specifically, transition T13 is from state 110 to state 130, and transition T31 is from state 130 to state 110. Transition T15 is from state 110 to state 150, and transition T51 is from state 150 to state 110. Transition T12 is from state 110 to state 120, and transition T21 is from state 120 to state 110. Transition T61 is from state 160 to state 110, and transition T26 is from state 120 to state 160. Transition T23 is from state 120 to state 130, and transition T24 is from state 120 to state 140. Transition T43 is from state 140 to state 130.

The behavior within each state is described above, but can take several potential functional forms. An example of torque functions that provide appropriate behaviors within each state is given in Table 1, which shows below.

TABLE 1

Finite state Torque Control Laws

| FSM State | | Torque Control Law |
|---|---|---|
| 1 | $\tau_K = f_1(\dot{\theta}_K)$ | $\tau_K = C_1\dot{\theta}_K^2$ |
| 2 | $\tau_K = f_2(\omega, \dot{\theta}_K)$ | $\tau_K = C_2[\omega - \omega_0]\dot{\theta}_K$ |
| 3 | $\tau_K = f_3(\omega, \theta_K, \dot{\theta}_K)$ | $\tau_K = b_{max}[1 - e^{(\theta_K - C_{3\alpha} - C_{3\beta}\omega)/C_{3\gamma}}]\dot{\theta}_K$ |
| 4 | $\tau_K = f_4(\omega)$ | $\tau_K = C_4[1 - \omega/\omega_0]$ |
| 5 | $\tau_K = f_5(F, \theta_K)$ | $\tau_K = C_{5\alpha}F \sin \theta_K[1 - e^{\dot{\theta}_T/C_{5\beta}}][1 - e^{-t/C_{5\gamma}}]$ |
| 6 | $\tau_K = f_6(\theta_K, \dot{\theta}_K, \theta_T)$ | $\tau_K = C_{6p}[\theta_K - \theta_{EQ}(\theta_T)] + C_{6d}\dot{\theta}_K$ |

For the behaviors described in Table 1, each torque control law is based upon a combination of sensor inputs, including knee angle ($\theta_K$) and velocity ($\dot{\theta}_K$), thigh angle ($\theta_T$), equilibrium angle of a virtual spring ($\theta_{EQ}$), shank axial force (F), and walking speed estimation ($\omega$). Each torque control law ($f_n$) has between one and three tunable parameters ($C_n$). For $f_3$, $b_{max}$ indicates the maximum achievable motor braking impedance (i.e., when all motor leads shorted together). For $f_2$ and $f_4$, $\omega_0$ indicates the crossover walking speed, which is the walking speed where the motor provides neither assistance nor resistance and swing-flexion motion is governed by passive dynamics alone. As such, $f_2$ and $f_4$ provide a continuum of swing-flexion behavior, based on the observation that the amount of energy dissipated during the swing-flexion phase of gait as a function of the walking speed (see FIG. 7A, which is discussed below), that adjusts the amount of resistance or assistance at the knee joint to achieve a desired amount of energy dissipation during swing-flexion.

Table 2 is shown below that includes controller sequences for different activities.

TABLE 2

| Controller Sequence for Different Activities | |
|---|---|
| FSM State Sequence (of FIG. 2) | Functional Activities |
| 110 | Standing; stand-to-sit; backwards walking |
| 110-120-130 | Level-ground and up-slope walking |
| 110-120-140-130 | Slow walking (level-ground and up-slope) |
| 110-130 | Down-slope and down-stair walking |
| 110-150 | Sit-to-stand |
| 110-120-160-110-150 | Up-stairs walking |

Depending on the activity being performed, the controlling unit produces state sequences, as appropriate for that activity. Table 2 above shows the state sequences for different activities. For most walking activities, the state sequence will be states 110-120-130, while down-slope and down-stair walking, the sequence will be states 110-130. For slow walking (level-ground and up-slope) the sequence will be states 110-120-140-130, where state 140 will add flexion assistance during swing to increase knee flexion and toe clearance. For stair ascent (up-stairs walking), the sequence will be states 110-120-160-110-150, where state 160 provides a prescribed powered swing motion and state 150 provides stance-knee extension assistance. The sit-to-stand sequence of transitions is states 110-150; while standing, stand-to-sit, and backwards walking remain in state 110. Each activity includes at least the state 110 (passive stance-resistance state). As such, every activity includes at least one passive state; alternatively stated, no activity is comprised of strictly powered states.

The controlling unit selects the control state based on the transition conditions, which are selected to appropriate behaviors corresponding to various activities. Transition conditions in one embodiment are described in Table 3, which are based on onboard sensing of knee angle ($\theta_K$), shank angle ($\theta_S$), shank axial force (F), shank axial acceleration ($a_a$), the walking speed estimation ($\omega$), and a state timer (t).

Table 3 is shown below.

TABLE 3

| Finite State Machine Transition Conditions | | |
|---|---|---|
| Transition | Description | Condition |
| $T_{12}$ | Knee joint is hyperextended, and | $\theta_K \approx 0$ |
| | Prosthesis shank is rotating forward, and | $\dot{\theta}_S < \dot{\theta}_{S,th}$ |
| | Prosthesis shank is inclined forward, and | $\theta_S < \theta_{S,th}$ |
| | Prosthesis is rapidly unloaded | $\dot{F} < \dot{F}_{th}$ |
| $T_{23}$ | Prosthesis is unloaded, and | $F \approx 0$ |
| | Knee joint is extending | $\dot{\theta}_K > 0$ |
| $T_{31}$ | Knee joint has zero velocity, or | $\dot{\theta}_K \approx 0$, or |
| | Prosthesis is loaded | $F > F_{th}$ |
| $T_{13}$ | Prosthesis is unloaded, and | $F \approx 0$ |
| | Knee joint is flexed above threshold | $\theta_K > \theta_{K,th}$ |
| $T_{21}$ | Prosthesis is loaded, and | $F > F_{th}$, and |
| | Prosthesis was previously unloaded, or | $F^- \approx 0$, or |
| | Prosthesis shank rotating backwards, or | $\dot{\theta}_S > \dot{\theta}_{S,th}$, or |
| | Prosthesis shank is not inclined forward | $\theta_S > \theta_{S,th}$ |
| $T_{24}$ | Knee joint begins flexing, and | $\theta_K > 0$ |
| | Slow walking speed detected, and | $\omega < \omega_0$ |
| | Walking speed above threshold | $\omega > \omega_{th}$ |
| $T_{43}$ | Prosthesis is unloaded, and | $F \approx 0$ |
| | Knee joint is extending | $\dot{\theta}_K > 0$ |
| $T_{15}$ | Knee joint is flexed past threshold, and | $\theta_K > \theta_{K,th}$ |
| | Knee joint is extending | $\dot{\theta}_K < 0$ |
| $T_{51}$ | Knee joint is fully extended, or | $\theta_K \approx 0$, or |
| | Knee joint is flexing | $\dot{\theta}_K > 0$ |
| $T_{26}$ | Knee joint is hyperextended, and | $\theta_K \approx 0$ |
| | Prosthesis is unloaded, and | $F \approx 0$ |
| | Shank axial acceleration above threshold | $\alpha_\alpha > \alpha_{\alpha,th}$ |
| $T_{61}$ | Prosthesis is loaded, or | $F > F_{th}$, or |
| | Time in state beyond threshold | $t > t_{th}$ |

The transition conditions of the controlling unit depend upon measured sensor inputs and several threshold parameters: knee angle ($\theta_{K,th}$), shank angle ($\theta_{S,th}$) and angular velocity ($\dot{\theta}_{S,th}$), shank axial force ($F_{th}$) and yank ($\dot{F}_{th}$), walking speed estimation ($\omega_{th}$), shank axial acceleration ($\alpha_{\alpha,th}$) and time ($t_{th}$).

States 110 and 150 provide the necessary mechanical power dissipation and generation during stance-phase to accomplish a variety of functional activities. Turbulent damping via passive motor control provides knee-yielding akin to a microprocessor-controlled knee (MPK) so as to provide resistance to knee buckling during level-ground walking and to provide an appropriate knee motion during down-slope and down-stairs walking, as well as stand-to-sit. The active stance control law, which consumes battery power to provide an active assistance torque, generalizes powered knee extension into a single torque control law that is adaptive across a range of activities that benefit from positive joint power. The control law was developed from observations of the interaction between the biological knee and hip joints during stair ascent.

Referring to FIGS. 3A-3E, the torque, velocity, and power of the biological knee joint lag behind those of the hip joint during stair ascent. The torque command in Table 1 was designed to input force and motion estimates of the residual hip joint and reproduce the shape and timing of the torque profile of the biological knee joint, but without commanding a desired joint angle, which would otherwise have the knee prosthesis, rather than the user, control knee motion. During the pull-up phase of stair ascent, the prosthetic ankle constrains the shank to be approximately vertical. As such, the real-time hip torque is estimated as the product of the load cell force and the sine of the knee angle (see FIG. 3E). The thigh velocity and knee angle terms in the control law (see Table 1) provide for the bell shape of the torque command, and the filtering term provides the phase delay between hip and knee kinetics and kinematics. Ideally, the parameters $C_{5\beta}$ and $C_{5\gamma}$ are invariant between users, providing the torque control law a single parameter ($C_{5\alpha}$) that increases or decreases the magnitude of assistive torque, depending on the user's preference.

Figure 3A:
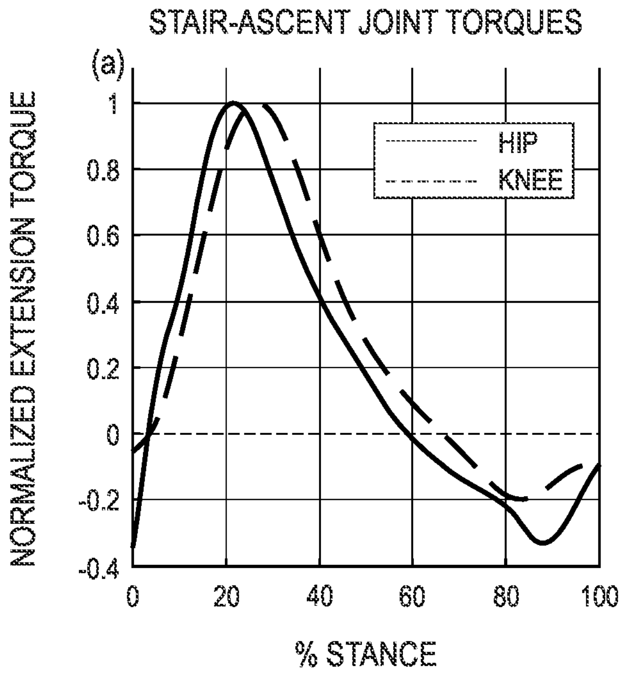
FIG. 3A is a graph of a stair-ascent joint torques showing normalized extension torques versus stance percentages.
Figure 3B:
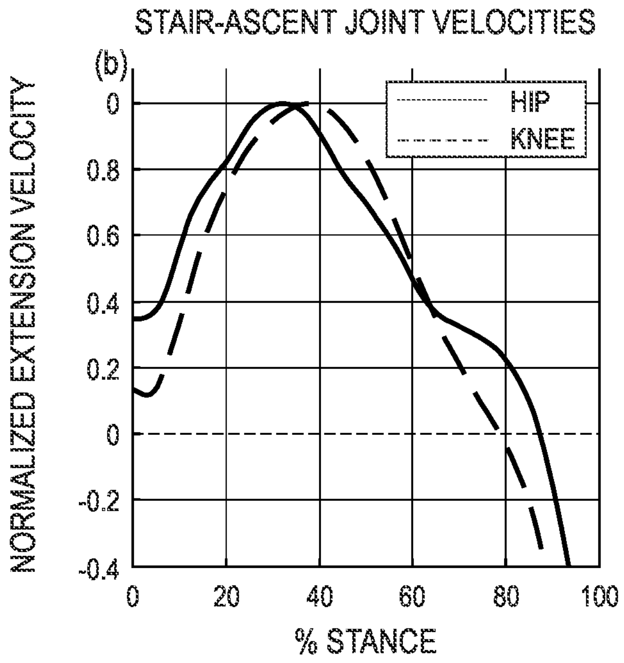
FIG. 3B is a graph of a stair-ascent joint velocities showing normalized extension velocities versus stance percentages.
Figure 3C:
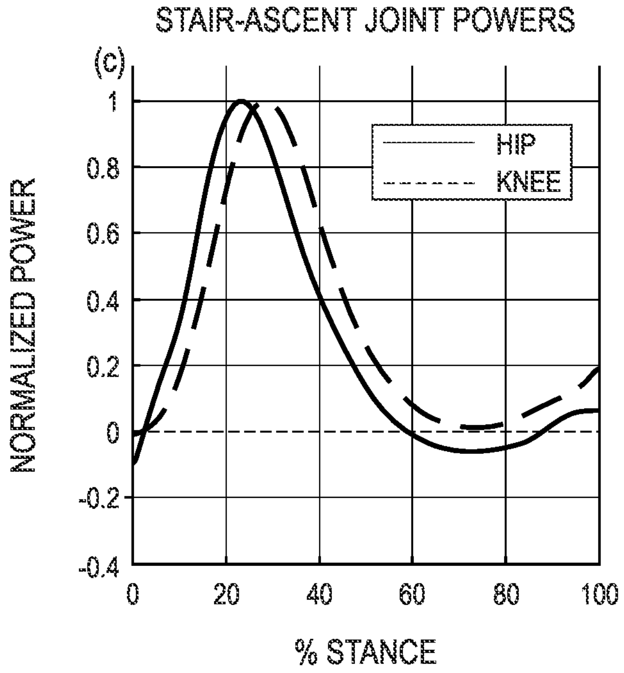
FIG. 3C is a graph of a stair-ascent joint powers showing normalized power versus stance percentages.
Figure 3D:
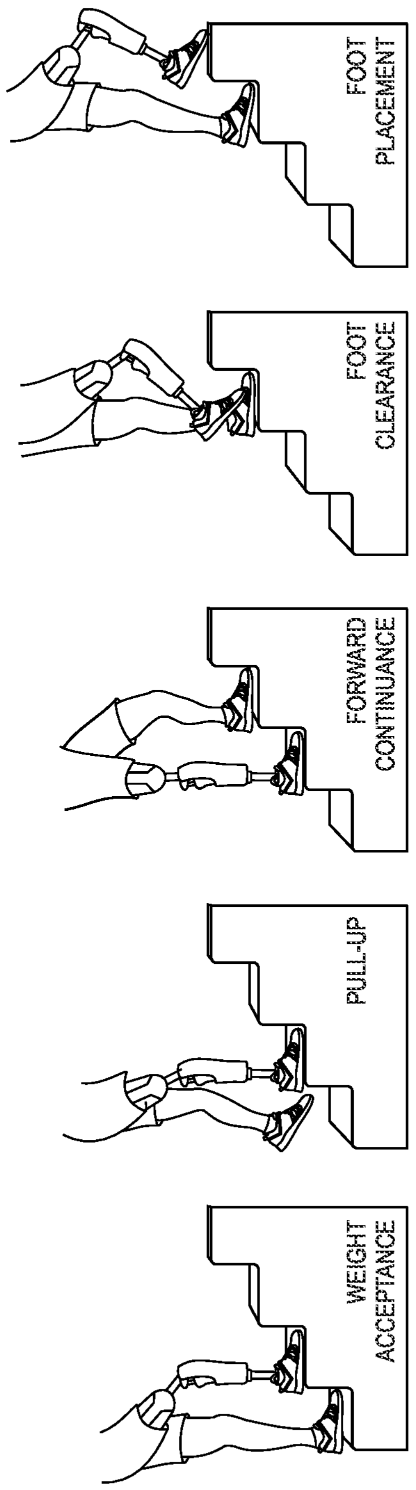
FIG. 3D is a sequence of different phases of a user with a powered knee prosthesis ascending stairs.
Figure 3E:
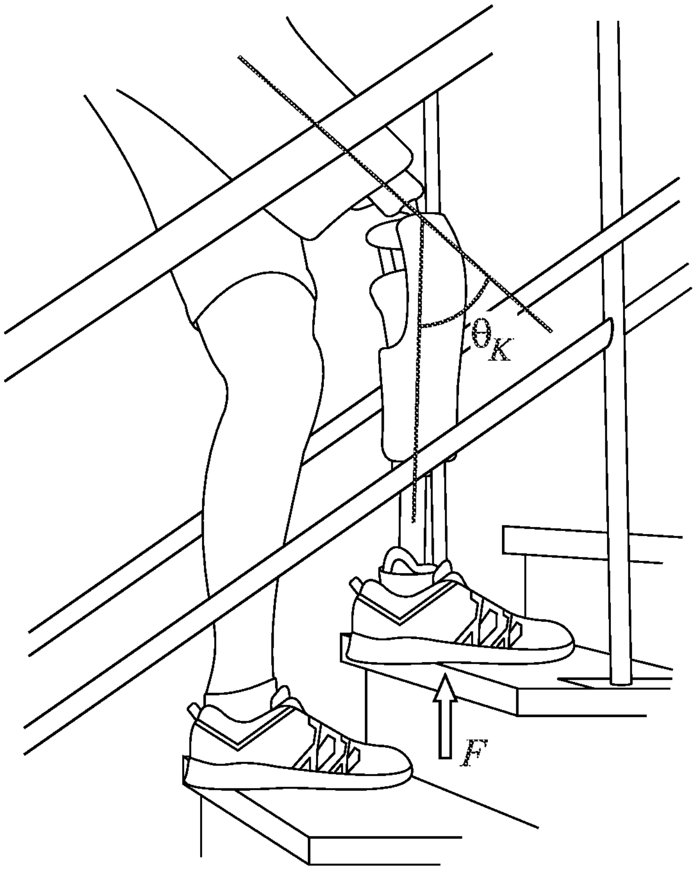
FIG. 3E shows a powered knee prosthesis with a sine of a knee angle ($\theta_K$) and showing a load cell force (F).

Referring to FIGS. 3A-3C, a stance-phase torque, velocity and power of knee and hip joints during the stance-phase of stair ascent are shown respectively. The y-axes of FIGS. 3A-3C indicate (a) extension torque, (b) extension velocity, and (c) power generation, respectively. Values are normalized to a maximum of unity and thus, are dimensionless. These charts or plots demonstrated that the phasing of the knee joint lags the hip joint for most of the stance-phase. FIG. 3D shows various phases of stair ascent. Referring to FIG. 3E, when ascending stairs with a stiff prosthetic foot, the shank is constrained to be approximately vertical. The hip torque can be approximated by onboard sensors as the product of the load cell force (F) and the sine of the knee angle ($\theta_K$). The controlling unit uses this approximation of hip torque to deliver knee torque that is synchronized with the user's motion.

In one desired embodiment, the knee prosthesis provides little to no resistance in the extension direction, which enables the user to extend the stance leg via hip musculature without drivetrain resistance. Because the prosthetic foot is frictionally constrained to the ground during stance-phase, the stance leg is a closed kinematic chain, and therefore the user has control of knee joint movement during the stance-phase via movement of the hip joint. The user is therefore able to extend the knee joint without power-assistance, albeit with disproportionate hip torque input from the user. In the knee prosthesis system described here, powered knee extension is activated by the user via hip torque, which initiates a knee extension movement, which in turn is identified by the controlling unit and used to initiate power-assisted knee extension. Because the user is able to volitionally control the activation of powered stance knee-extension, intent recognition algorithms are not necessary for coordinated control since the coordination is inherent because power delivery is solely in reaction to the motion input generated by the user.

Additionally, the thigh velocity term in the torque control equation scales torque delivery with estimated thigh power. Just as the biological hip and knee work synergistically to extend the leg when it is in a closed kinetic chain, the knee prosthesis is able to follow motion and force cues from the residual hip (under the user's neuromuscular control) and provide synchronous assistive knee torque. In this manner, a user does not ride the knee prosthesis up the stairs, but rather works with it to extend the leg, similar to the manner in which an electric bicycle coordinates its power delivery with the user's power input. While it is possible to cause controller instability using such a method, since a velocity term is used in the torque control law to add energy, instability is avoided by the combination of making the control law unidirectional, using an exponential decay as a soft saturation on the velocity term, and using the sine of the knee angle to decay the torque as the knee extends. With this control law formulation, if the user stops extending their hip, the user's mass decelerates the knee joint, which reduces the torque and continues the deceleration. When knee velocity inflects, the controlling unit switches to resistive stance behavior, providing controlled support of the user's weight as the knee flexes.

Figure 4A:
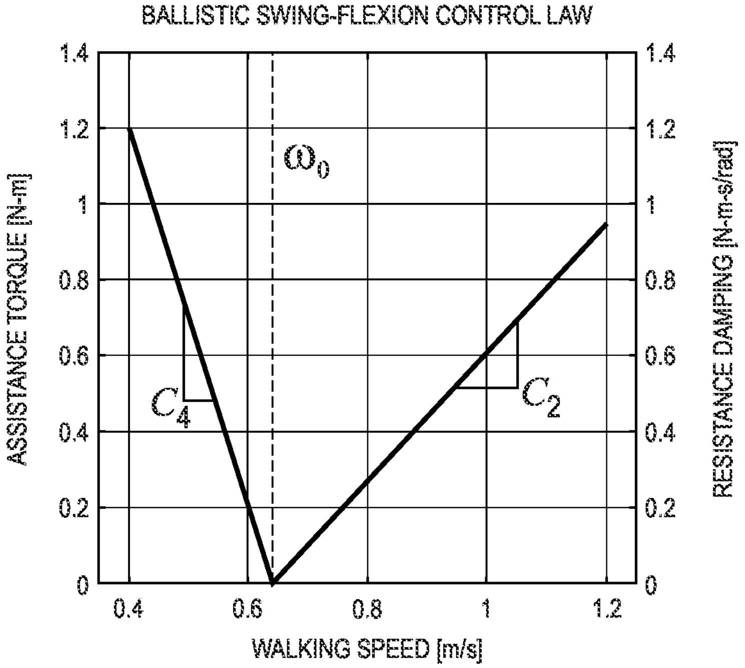
FIG. 4A is a graph of ballistic swing-flexion control law showing the continuum of assistance torque and resistance coefficient versus walking speed.
Figure 4B:
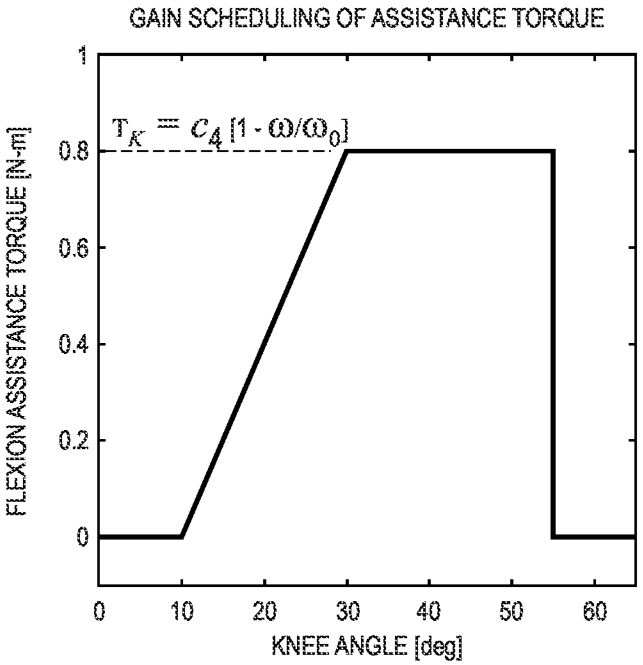
FIG. 4B is a graph of gain scheduling of assistance torque showing flexion assistance torque versus knee angle.
Figure 4C:
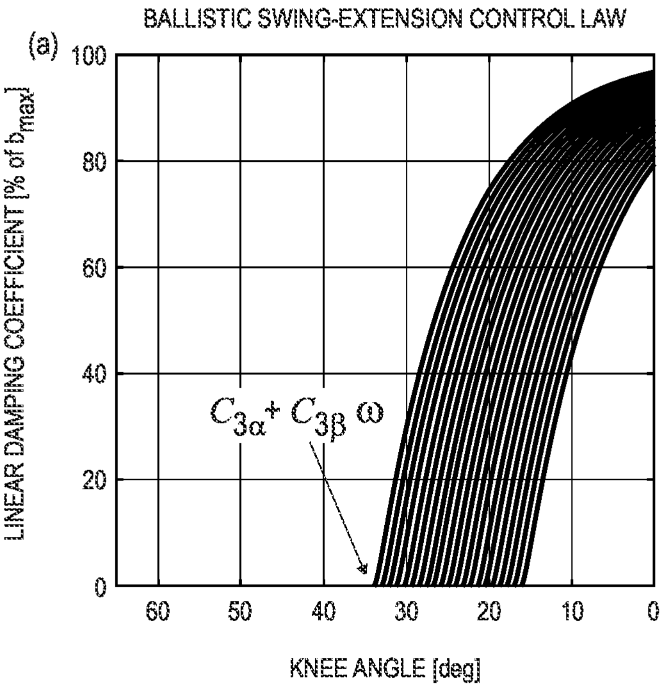
FIG. 4C is a graph of ballistic swing-extension control law showing linear damping coefficient versus knee angle.

The states 120, 130 and 140 provide walking-speed-adaptive ballistic swing phase behavior as shown in FIGS. 4A-4C. These states provide low-torque assistive or resistive behaviors as a function of the estimated walking speed (see Table 1). To estimate the walking speed, the shank angular velocity is recorded and averaged from foot contact until a user initiates swing-phase in late-stance. The result is a linear relationship between the value of the average stance-phase shank angular velocity ($\omega$) and the walking speed. As such, w is a zero-parameter term that measures relative changes in walking speed within a single stride and may be used directly in control equations to provide cadence-adaptive behavior.

During swing-flexion, the knee joint must provide an amount of resistance that: (1) achieves an adequate flexion angle, based on the leg geometry, that provides robust toe-clearance as the thigh swings forward, (2) prevents unnecessary motion of the knee joint by limiting the maximum flexion angle (i.e., too much knee flexion unnecessarily increases the duration of swing-phase), and (3) achieves timing of the peak-flexion knee angle such that the effective length of the leg is shortest when oriented vertically (i.e. the knee is flexed most when the toe is directly under the pelvis). During swing-extension, the knee joint must provide an amount of resistance that: (1) is sufficiently low in early swing-extension, such that inertial forces can rapidly accelerate the joint velocity, (2) is sufficiently high in terminal swing, such that a sufficient amount of kinetic energy is dissipated to make impact forces at full-extension negligibly small, and (3) provides a resistive torque profile that minimizes socket reaction forces as the magnitude of resistive torque increases.

Figure 5A:
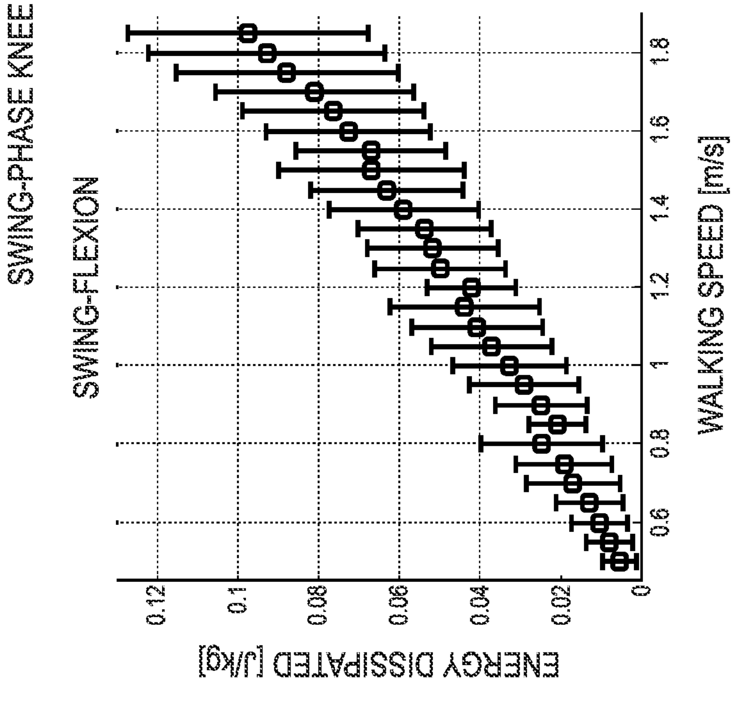
FIG. 5A is a graph showing energy dissipation during a swing-flexion phase of level-ground walking at various walking speeds.
Figure 5B:
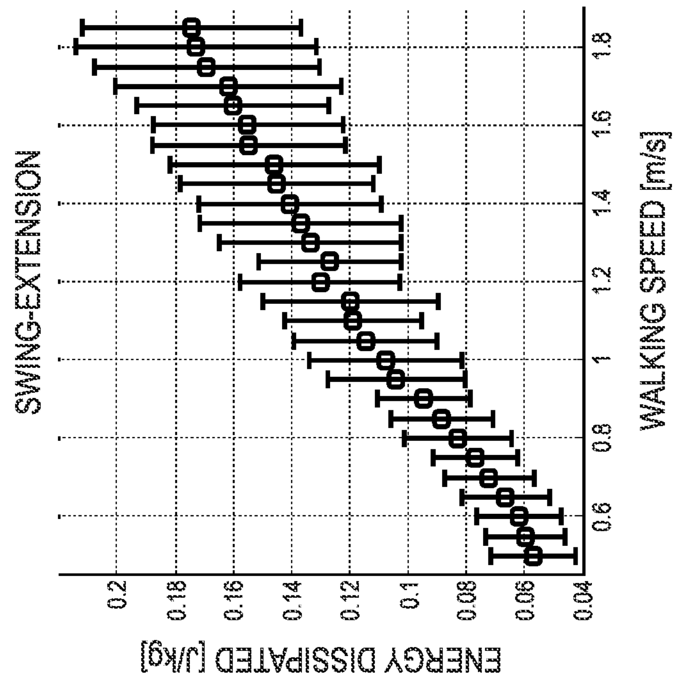
FIG. 5B is a graph showing energy dissipation during a swing-extension phase of level-ground walking at various walking speeds.

FIGS. 5A, 5B shows energy dissipation versus walking speed during the swing-flexion and swing-extension phases of level-ground walking. The behavior of the healthy knee during the swing-phase of level-ground walking was characterized based on observations made from a set of data representing 22 healthy subjects. The box-and-whisker plots indicate mean and standard deviation of 22 subjects. Using this data, the amount of energy dissipated by the knee joint during the flexion and extension portions of swing phase, respectively, was computed and plotted against walking speed, as shown in FIGS. 5A, 5B.

As indicated in FIGS. 5A, 5B, the energy dissipated within each portion of swing can be reasonably modeled as respective linear functions of walking speed. The swing-flexion and swing-extension torque control laws were designed to dissipate an amount of energy as a function of the estimated walking speed. There is an approximate linear relationship between energy dissipation and walking speed. The knee joint produces net negative work for most walking speeds during swing-flexion and all walking speeds during swing-extension. This observation is the basis of the torque control laws for states 120, 140.

During swing-flexion, when estimated walking speeds are above the crossover walking speed (i.e., when $\omega > \omega_0$), a damping torque is provided, similar to a MPK. When $\omega < \omega_0$, a feedforward assistive flexion torque is provided, which increases the peak-flexion knee angle to a biomimetic value not achievable with passive dynamics alone. This assistive torque has low amplitude and is provided unidirectionally, without trying to control knee angle directly, which enables a swing-phase motion that is still inertially-coupled (i.e., ballistic swing is preserved because low actuator impedance makes the knee joint receptive to inputs from inertial forces), but with the caveat that the motor is helping the user by "pushing" the lower leg towards flexion. Furthermore, the assistive torque gains are scheduled as a function of the knee joint kinematics, such that the user must first initiate a swing-flexion motion before receiving powered assistance from the motor. This powered assistance is low in magnitude and, when integrated over the range of motion of the swing-flexion phase, increases the total energy at the knee joint, which reduces the amount of net energy dissipated by the joint impedance. In this manner, actuator impedance compensation is achieved via low-bandwidth energy compensation.

The state 130 (swing-extension state) provides cadence-adaptive ballistic swing-extension behavior (see FIG. 4C), which is appropriate for the swing-extension phase of all state machine walking activities except for stair ascent, which requires non-ballistic swing. For level and up-slope walking, swing-extension behavior is provided immediately after peak-flexion. For down-slope and down-stairs walking, swing-extension behavior is provided when the user lifts the flexed prosthetic knee, allowing inertial and gravitational forces to provide the extensive torque.

Referring to FIGS. 4A-4C, ballistic swing torque control laws, incorporating both assistive and resistive behaviors are shown. In FIG. 4A, during swing-flexion, for walking speeds below $\omega_0$, an assistive torque is provided. For walking speeds above $\omega_0$, a resistive torque is provided. Both torque control laws are linearly proportional to walking speed, which provides cadence-adaptive behavior. FIG. 4B shows gain scheduling of swing-flexion assistance torque. After the user has flexed the knee joint past 10 degrees, the assistance torque begins ramping up to the commanded value as a function of knee angle. At 30 degrees of flexion, the assistance torque has reached its commanded value. After 55 degrees of flexion, the commanded torque is zeroed so the knee joint velocity can inflect for swing-extension.

Referring to FIG. 4C, the swing-extension torque control law commands a linear damping torque where the linear damping coefficient is a function of the walking speed and the knee angle (the walking speeds are located on the left side of the graph, while the faster speeds are located on the right side of the graph). The commanded torque is zero until a predetermined angle that is a function of the walking speed estimation ($C_{3\alpha}+C_{3\beta}\omega$). After this point, the damping coefficient rapidly increases towards the maximum value ($b_{max}$). An exponential curve serves as a soft saturation of knee damping.

The state 160 (powered swing state) provides non-ballistic swing-phase motion appropriate for stair-ascent. The state 160 passes through the state 120, ensuring that powered swing is provided as a transition from late-stance similar to other walking conditions. This controller creates a virtual linkage between the thigh and shank, which enables the user to volitionally control the knee joint. To contrast ballistic and non-ballistic swing controllers, the former is controlled through inertial coupling while the latter is controlled through kinematic coupling.

EXAMPLES

An experimental assessment was performed with the intent of demonstrating: (1) the ability of the control system to provide cadence-adaptive ballistic swing-phase control based on dissipating a predetermined amount of kinetic energy for each walking speed; and (2) the ability of the control system to seamlessly transition between activities and provide passive or powered functionality as appropriate for the activity. The experimental assessments consisted of two tests: (1) treadmill walking on level-ground at nine treadmill speeds between 0.4 and 1.2 m/s; and (2) walking in an over-ground circuit with level-ground, ramps, stairs, and sitting/standing. The assessments were conducted on a single subject with transfemoral amputation-a 62-year old male, weighing 85 kg, who used an Ottobock C-Leg 4 (Comparative MPK) as his daily-use prosthesis.

In the first experiment, the subject first conducted the protocol wearing the Comparative MPK, then followed the same protocol wearing the Inventive prosthesis knee with the powered-on passive controlling unit ("Inventive prosthesis knee"). Knee angle data were recorded via a motion capture system (Vicon), and ground reaction force was recorded via force plates integrated into either a Bertec instrumented treadmill. The subject was allowed to reach steady-state before motion capture data were recorded, and 15 strides of steady-state walking were recorded for each walking speed. The subject rested five minutes between trials.

In the second experiment, the subject completed a single loop through a circuit that included level-ground, turns, ramps, stairs, and sitting/standing with a chair. Knee angle and controller state data were recorded using the embedded system. This circuit was only completed once to demonstrate the ability of the controlling unit to adapt to a variety of activities with the control system and demonstrate how the finite state machine cycles through states during each activity and while making transitions between activities.

Figure 6A:
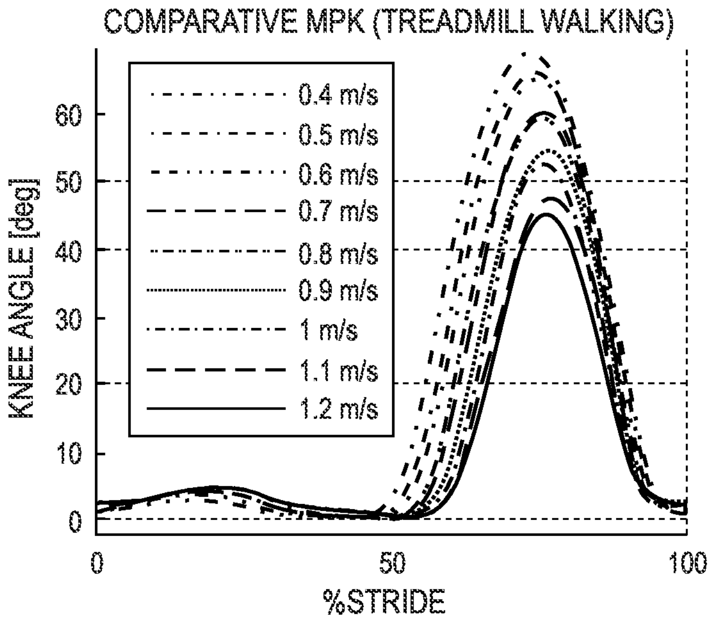
FIG. 6A is a graph of a comparative microprocessor-controlled knee (MPK) showing knee angle versus stride percentage.
Figure 6B:
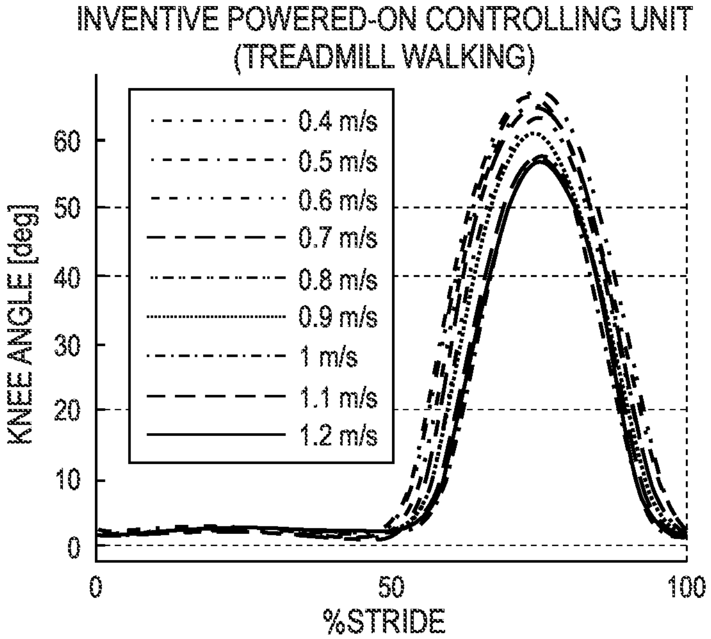
FIG. 6B is a graph of an inventive powered-on passive controlling unit showing knee angle versus stride percentage.
Figure 6C:
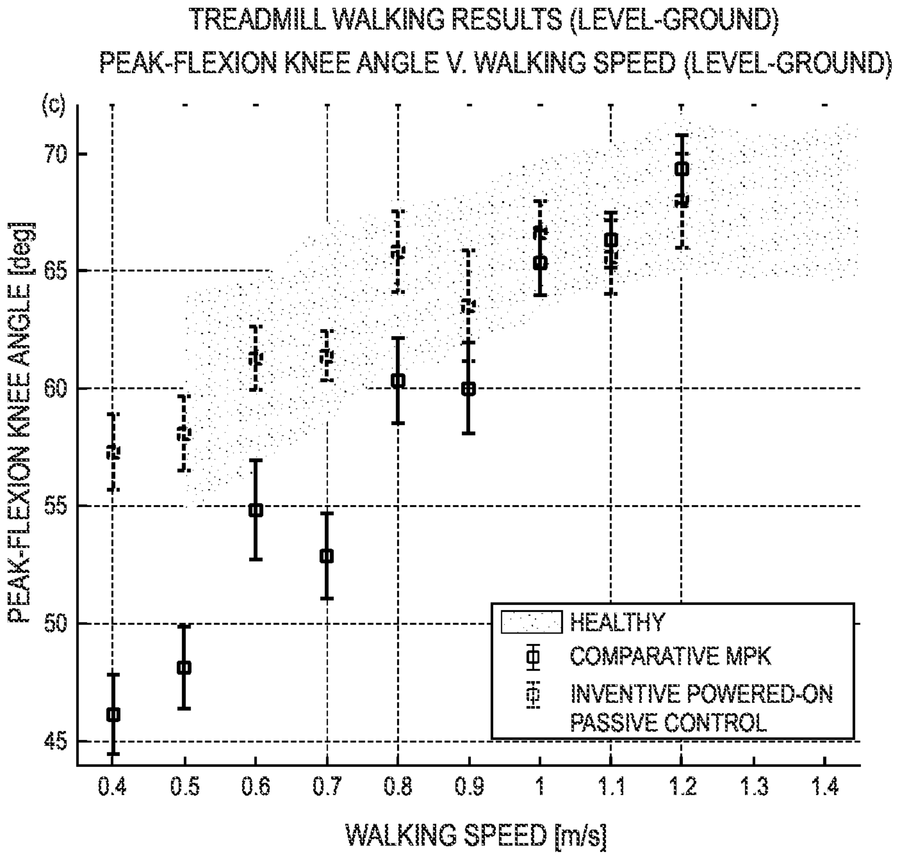
FIG. 6C is a graph of peak-flexion knee angle versus walking speed of a healthy individual, the comparative MPK of FIG. 6A and the inventive powered-on passive controlling unit of FIG. 6B.

Referring to FIGS. 6A-6C, experimental results showed 15-stride average knee angle of the Comparative MPK (FIG. 6A) and the Inventive prosthesis knee (FIG. 6B) in level-ground walking at walking speeds between 0.4 to 1.2 m/s.

During level-ground walking, the stance and swing phase kinematics were highly similar between the Inventive prosthesis knee and the Comparative MPK across speeds. FIGS. 6A, 6B show the knee angle of the Inventive prosthesis knee and the comparative MPK as a function of stride for a range of walking speeds during level-ground walking. On both prosthetic knees, the knee joint remained extended during the stance-phase and flexed to an angle between 40 and 70 degrees in the swing-phase, depending on walking speed. The swing-phase trajectory of each prosthetic knee has a bell shape of similar duration for each walking speed and slope.

FIG. 6C showed peak-flexion knee angle versus walking speed during level-ground walking, comparing the Inventive prosthesis knee to the Comparative MPK and control data from healthy subjects (with shaded gray dots). The box-and-whisker plots indicated 15-stride mean and standard deviation of the peak swing-flexion knee angle for each walking speed in level-ground walking. Shaded grey areas indicated range of one standard deviation of averaged maximum knee angle data from 28 healthy subjects.

FIG. 6C shows the peak-flexion knee angle of both prostheses across walking speeds during level-ground walking, along with corresponding data from healthy subjects. As shown in FIG. 6C, between 0.8 and 1.2 m/s, the peak-flexion knee angles were similar between prosthetic knees (Comparative MPK and the Inventive prosthesis knee). In FIG. 6C, both prostheses show a trend of increasing peak-flexion knee angle with increasing walking speed.

The Comparative MPK, however, deviated from healthy data at walking speeds below 0.8 m/s. The peak-flexion knee angles of the Inventive prosthesis knee more closely matched the healthy data as compared to the Comparative MPK. During slow walking, swing-assistance torque increased the peak-flexion knee angle to biomimetic levels, which would otherwise not be achievable using passive dynamics alone. This increased knee flexion can potentially reduce the compensatory motion required by the user to avoid catching the toe of the prosthesis during slow walking, since most prosthetic feet cannot actively dorsiflex like the biological ankle does during swing-phase.

Figure 7A:
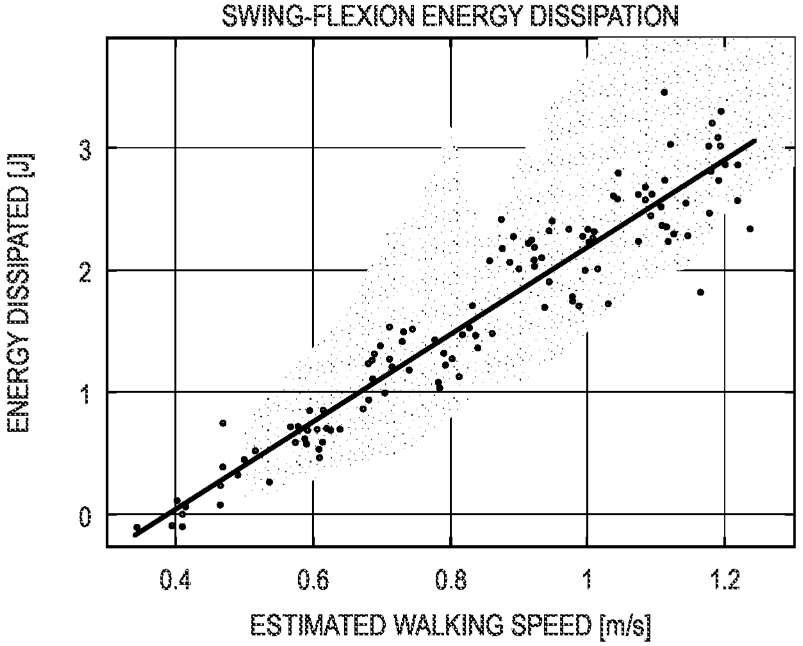
FIG. 7A is a plot of swing-flexion energy dissipation versus estimated walking speed.
Figure 7B:
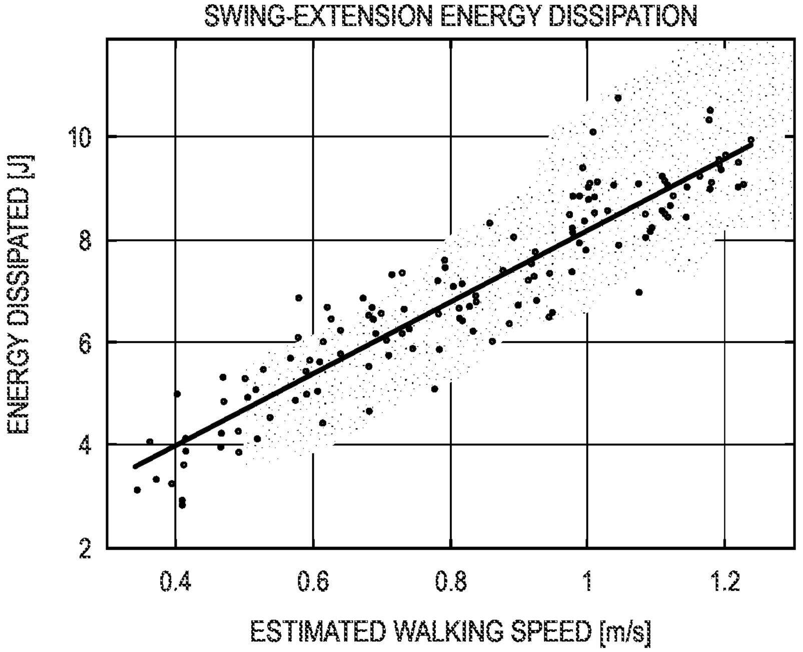
FIG. 7B is a plot of swing-extension energy dissipation versus estimated walking speed.

The ballistic swing control laws in Table 1 were formulated to dissipate an amount of energy appropriate for the estimated walking speed in both swing-flexion and swing-extension. FIGS. 7A, 7B show the energy dissipated during swing-phase a calculated by the embedded system using recorded sensor data and a model of actuator impedance. Energy dissipation is linear with respect to walking speed for both swing-flexion and swing-extension and is within the range of healthy data from FIGS. 7A, 7B (note that the data has been scaled to match the bodyweight of the test subject).

Specifically, FIGS. 7A, 7B show swing-phase energy dissipation versus estimated walking speed. These plots showed the estimated energy dissipation at the knee joint (calculated from motor torque, actuator kinematics, and a model of actuator impedance). The dots represented the energy and walking speed of each stride, the solid line indicated the linear regression of individual stride data; and shaded grey areas indicated the data from healthy subjects shown in FIGS. 5A, 5B.

The data in FIG. 7A, 7B for knee joint energetics and the data in FIGS. 6A-6C for knee joint kinematics indicated that the swing-flexion torque control laws (both resistive and assistive) achieved the kinematic goals by meeting energetic goals. By dissipating an amount of energy appropriate for the walking speed, the knee joint achieved a desired peak flexion magnitude with appropriate phasing of that peak magnitude.

Figure 8A:
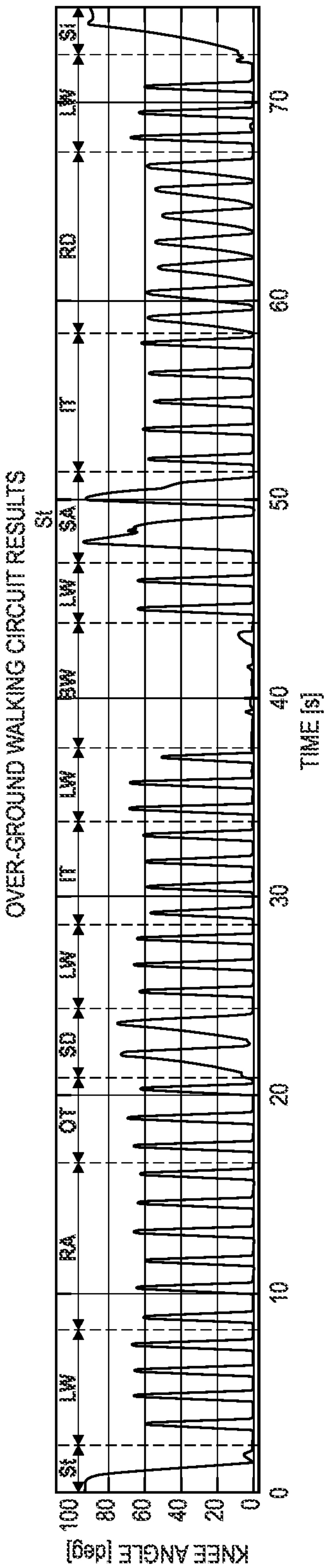
FIG. 8A is a graph of over-ground walking circuit results showing knee angle versus time.
Figure 8B:
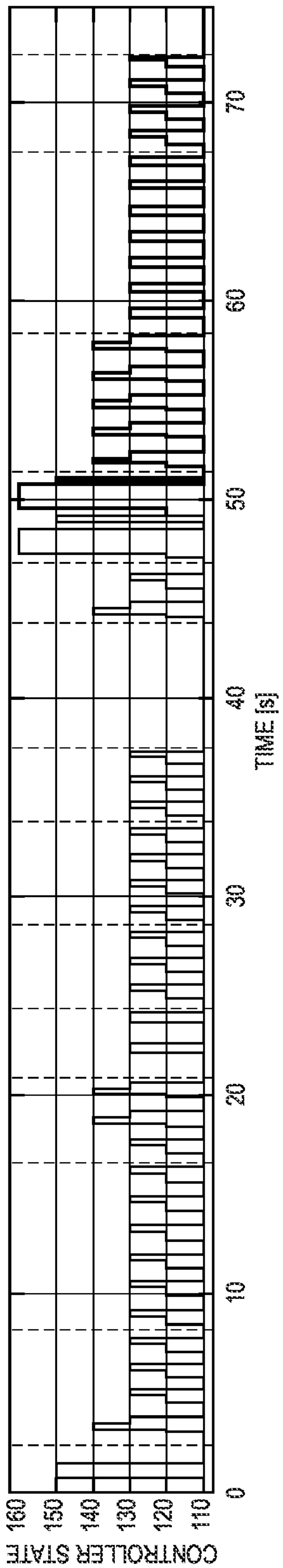
FIG. 8B is a graph of over-ground walking circuit results showing states of the controlling unit versus time.

The overground walking circuit demonstrates the ability of the FSM of FIG. 2 to provide appropriate behavior across the range of activities listed in Table 2 with seamless transitions between activities. FIG. 8A, 8B showed the results of an over-ground walking circuit, where a subject performed a variety of activities with the Inventive prosthesis knee. FIGS. 8A, 8B showed both knee angle and controller state as a function of time to demonstrate the state-flow of the controlling unit within and between each activity and the corresponding knee motion.

FIG. 8A reflects the following sequence of activities: standing up from a chair ("St"), level ground walking ("LW"), ramp ascent ("RA"), outside turn ("OT"), stair descent ("SD"), level ground walking ("LW"), inside turn ("IT"), level ground walking ("LW"), backward walking ("BW"), level ground walking ("LW"), stair ascent ("SA"), inside turn ("IT"), ramp descent ("RD"), level ground walking ("LW"), and sitting ("Si").

FIG. 8B showed the state-flow during activities and between activities, demonstrating the manner in which the controlling unit is able to achieve the suite of appropriate passive and powered behaviors. No hesitation or special movement was required between activities suggesting that the transition conditions provided for automatic transitions based upon how a user moved the prosthesis. To transition to down-slope or down-stairs requires the same user motion as required by the Comparative MPK to utilize stance yielding; to transition to up-stairs, the subject unloaded the prosthesis with an extended knee while stepping up with his contralateral leg. To initiate powered sit-to-stand, the user needed only begin extending his hip while loading the prosthesis. In addition to providing appropriate gait activity (i.e., the appropriate sequence of passive and powered behaviors during an activity), the controlling unit permitted all transitions between activities to be facilitated through natural user motion. This control structure therefore enabled the user to perform a range of locomotion activities that leverage passive behaviors as much as possible, and layering in powered behaviors in response to user movements only when such powered behaviors are required. The result is a controlling unit that maximizes user control and agency over movement, while also minimizing the electrical power requirements associated with these movements.

Results of the over-ground walking circuit of FIGS. 8A, 8B showed (a) knee angle and (b) controller state for the entire circuit. For LW, RA, IT, and OT, the state flow was states 110-120-130. For slow walking, the state flow was states 110-120-140-130. For RD and SD, state flow was states 110-130. For SA, state flow was states 110-120-160-110-150.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above-described embodiment, method, and examples, but by all embodiments and methods within the scope and spirit of the invention.

What is claimed is:

1. A knee prosthesis system comprising:

a knee prosthesis including a thigh segment and a shank segment;

at least one actuator rotatably connecting the shank segment and the thigh segment, the at least one actuator being configured to controllably assume a powered knee behavior to generate knee motion or a passive knee behavior to resist knee motion; and a controlling unit including a finite-state control structure, the controlling unit electrically communicating with the at least one actuator, the control structure comprising at least three passive states and at least one powered state, the at least three passive states including a passive stance-resistance state, a passive swing-flexion state, and a passive swing-extension state, the at least one powered state including at least one of a powered swing-assistance state, a powered stance-assistance state, and a powered-swing state, wherein the passive stance-resistance state provides a high resistance against knee flexion, the passive swing-flexion state providing relative low resistance against knee flexion, the passive swing-extension state providing a low resistance against knee extension that increases substantially as a knee nears full extension, and wherein the powered swing-assistance state provides an assistive torque that flexes a knee joint, the powered stance-assistance state providing an assistive torque that extends the knee joint, and the powered-swing state providing a prescribed motion to the knee joint motion.

2. The knee prosthesis system of claim 1, wherein the at least one powered state is the powered swing-assistance state, the controlling unit selecting the swing-assistance state from the passive swing-flexion state based on detection of an entry condition, the controlling unit exiting the powered swing-assistance state into the passive swing-extension state upon detection of an exit condition.

3. The knee prosthesis system of claim 2, wherein the entry condition selecting the powered swing-assistance state from the passive swing-flexion state includes at least a detection of estimated walking speed less than a predetermined speed, the exit condition exiting the powered swing-assistance state into the passive swing-extension state includes at least a detection of a knee extension.

4. The knee prosthesis system of claim 2, wherein the resistance in the passive swing-flexion state and assistance in the powered swing-assistance state provides a net energy dissipation at a knee that increases continuously and monotonically as a function of estimated walking speed.

5. The knee prosthesis system of claim 1, wherein the at least one powered state is the powered stance-assistance state, the controlling unit selecting the powered stance-assistance state from the passive stance-resistance state based on detection of an entry condition, and the controlling unit exiting the powered stance-assistance state into the passive stance-resistance state upon detection of an exit condition.

6. The knee prosthesis system of claim 5, wherein an assistive extension knee torque provided is proportional to the estimated hip torque exerted by a user and estimated thigh angular velocity.

7. The knee prosthesis system of claim 1, wherein the at least one powered state is a powered-swing state, the controller selecting the powered-swing state from the passive swing-flexion state based on detection of an entry condition, and the controller exiting the powered-swing state into the passive stance-resistance state upon detection of an exit condition.

8. The knee prosthesis system of claim 7, wherein flexion knee assistance is a function of thigh angular velocity such that a knee will not initiate flexion until a thigh begins to flex.

9. The knee prosthesis system of claim 1, wherein the at least one powered state includes at least two of the powered swing-assistance state, the powered stance-assistance state, and the powered-swing state.

10. The knee prosthesis system of claim 9, wherein the at least one powered state includes all of the powered swing-assistance state, the powered stance-assistance state, and the powered-swing state.

11. The knee prosthesis system of claim 1, wherein the powered swing-assistance state is a function of knee angle such that the flexion assistance torque is not provided until the user begins to flex the knee.

12. The knee prosthesis system of claim 1, wherein the at least one actuator is a rotary actuator.

13. A knee prosthesis system comprising:

a knee prosthesis including a thigh segment and a shank segment;

at least one actuator rotatably connecting the shank segment and the thigh segment, the at least one actuator being configured to controllably assume a powered knee behavior to generate knee motion or a passive knee behavior to resist knee motion; and a controlling unit including a finite-state control structure, the controlling unit electrically communicating with the at least one actuator, the control structure comprising at least three passive states and at least one powered state, the at least three passive states including a passive stance-resistance state, a passive swing-flexion state, and a passive swing-extension state, the at least one powered state including at least one of a powered swing-assistance state, a powered stance-assistance state, and a powered-swing state, wherein the at least one powered state is the powered stance-assistance state, the controlling unit selecting the powered stance-assistance state from the passive stance-resistance state based on detection of an entry condition, and the controlling unit exiting the powered stance-assistance state into the passive stance-resistance state upon detection of an exit condition, wherein the entry condition selecting the powered stance-assistance state from the passive stance-resistance state includes at least detection of a knee joint extension, the exit condition exiting the powered stance-assistance state into the passive stance-resistance state includes at least detection of knee joint flexion.

14. A knee prosthesis system comprising:

a knee prosthesis including a thigh segment and a shank segment;

at least one actuator rotatably connecting the shank segment and the thigh segment, the at least one actuator being configured to controllably assume a powered knee behavior to generate knee motion or a passive knee behavior to resist knee motion; and a controlling unit including a finite-state control structure, the controlling unit electrically communicating with the at least one actuator, the control structure comprising at least three passive states and at least one powered state, the at least three passive states including a passive stance-resistance state, a passive swing-flexion state, and a passive swing-extension state, the at least one powered state including at least one of a powered swing-assistance state, a powered stance-assistance state, and a powered-swing state, wherein the at least one powered state is the powered stance-assistance state, the controlling unit selecting the powered stance-assistance state from the passive stance-resistance state based on detection of an entry condition, and the controlling unit exiting the powered stance-assistance state into the passive stance-resistance state upon detection of an exit condition, wherein the powered stance-assistance state provides an assistive knee extension torque that is a function of at least a measured force in the knee prosthesis and a measured angular velocity of the thigh segment.

15. A knee prosthesis system comprising:

a knee prosthesis including a thigh segment and a shank segment;

at least one actuator rotatably connecting the shank segment and the thigh segment, the at least one actuator being configured to controllably assume a powered knee behavior to generate knee motion or a passive knee behavior to resist knee motion; and a controlling unit including a finite-state control structure, the controlling unit electrically communicating with the at least one actuator, the control structure comprising at least three passive states and at least one powered state, the at least three passive states including a passive stance-resistance state, a passive swing-flexion state, and a passive swing-extension state, the at least one powered state including at least one of a powered swing-assistance state, a powered stance-assistance state, and a powered-swing state, wherein the at least one powered state is a powered-swing state, the controller selecting the powered-swing state from the passive swing-flexion state based on detection of an entry condition, and the controller exiting the powered-swing state into the passive stance-resistance state upon detection of an exit condition, wherein the entry condition selecting the powered-swing state from the passive swing-flexion state includes at least detection of a full knee joint extension when the knee prosthesis is unloaded, or axial acceleration of the shank segment above a threshold value when the knee prosthesis is unloaded, and wherein the exit condition includes at least detection of prosthesis loading.

16. A lower limb prosthesis comprising:

a foot prosthesis; and a knee prosthesis system including a thigh segment, a shank segment, at least one actuator and a controlling unit, the at least one actuator rotatably connecting the shank segment and the thigh segment, the at least one actuator being configured to controllably assume a powered knee behavior to generate knee motion or a passive knee behavior to resist knee motion, the controlling unit including a finite-state control structure, the controlling unit electrically communicating with the at least one actuator, the control structure comprising at least three passive states and at least one powered state, the at least three passive states including a passive stance-resistance state, a passive swing-flexion state, and a passive swing-extension state, the at least one powered state including at least one of a powered swing-assistance state, a powered stance-assistance state, and a powered-swing state, wherein the passive stance-resistance state provides a high resistance against knee flexion, the passive swing-flexion state providing relative low resistance against knee flexion, the passive swing-extension state providing a low resistance against knee extension that increases substantially as a knee nears full extension, and wherein the powered swing-assistance state provides an assistive torque that flexes a knee joint, the powered stance-assistance state providing an assistive torque that extends the knee joint, and the powered-swing state providing a prescribed knee joint motion.

* * * * *